(12) United States Patent
Peters et al.

(10) Patent No.: US 11,357,659 B2
(45) Date of Patent: Jun. 14, 2022

(54) SIDE SLEEPER ANTI-SNORING AND SLEEP APNEA PILLOW

(71) Applicants: Andre J. W. Peters, Winnipeg (CA); Rosa Peters, Winnipeg (CA)

(72) Inventors: Andre J. W. Peters, Winnipeg (CA); Rosa Peters, Winnipeg (CA); Simon Jervis, Whitby (CA)

( * ) Notice: Subject to any disclaimer, the term of this patent is extended or adjusted under 35 U.S.C. 154(b) by 315 days.

(21) Appl. No.: 16/550,686

(22) Filed: Aug. 26, 2019

(65) Prior Publication Data
US 2020/0085611 A1    Mar. 19, 2020

Related U.S. Application Data

(60) Provisional application No. 62/725,326, filed on Aug. 31, 2018.

(51) Int. Cl.
*A61F 5/56*     (2006.01)
*A47G 9/10*     (2006.01)

(52) U.S. Cl.
CPC .............. *A61F 5/56* (2013.01); *A47G 9/1081* (2013.01); *A47G 2009/1018* (2013.01)

(58) Field of Classification Search
CPC ......... A61F 5/56; A47G 9/1081; A47G 9/109; A47G 2009/1018; A47G 9/10; A61G 13/12; A61G 13/1205; A61G 13/121; A61G 13/1215; A61G 13/128; A61G 13/1295; A61G 7/065–07; A61G 7/072
See application file for complete search history.

(56) References Cited

U.S. PATENT DOCUMENTS

| | | | | |
|---|---|---|---|---|
| 3,694,831 A * | 10/1972 | Treace | ..................... | A47G 9/10 5/636 |
| 7,316,041 B2 * | 1/2008 | Guez | ........................ | A47G 9/10 5/636 |
| 8,677,531 B2 | 3/2014 | Popitz | | |
| 2012/0073057 A1 * | 3/2012 | Sramek | ................... | A47G 9/109 5/636 |
| 2012/0180220 A1 * | 7/2012 | Popitz | ................... | A47G 9/1081 5/636 |
| 2014/0317852 A1 * | 10/2014 | Chen | ..................... | A47G 9/109 5/644 |

* cited by examiner

*Primary Examiner* — Michelle J Lee
(74) *Attorney, Agent, or Firm* — Kyle R Satterthwaite; Ryan W Dupuis; Ade & Company Inc.

(57) ABSTRACT

A pillow for treating snoring and/or sleep apnea features at least one head recess having a bottom area for receiving and supporting a lateral side of a user's face, and a peripheral area spanning upwardly from the bottom area at a perimeter thereof. A neck channel extends from the head recess. The peripheral area of the head recess includes a chin region that reaches laterally outward from the neck channel at an angle and orientation such that the user's cervical spine resides in a relaxed non-extended state, and the user's mandible is maintained in a closed position. In embodiments for couples, first and second head recesses in the top of one pillow face inwardly toward one another, and third and fourth head recesses in either the bottom of the same pillow or the top of a separate pillow bottom surface face outwardly away from one another.

18 Claims, 7 Drawing Sheets

SIDE SLEEPER ANTI-SNORING AND SLEEP APNEA PILLOW

CROSS-REFERENCE TO RELATED APPLICATIONS

This application claims benefit under 35 U.S.C. 119(e) of U.S. Provisional Application No. 62/725,326, filed Aug. 31, 2018, the entirety of which is incorporated herein by reference.

FIELD OF THE INVENTION

The present invention relates generally pillows designed to place the head of a side-sleeping user in a suitable position for treating snoring and/or sleep apnea.

BACKGROUND

One such pillow of the aforementioned type is disclosed in U.S. Pat. No. 8,677,531 by Michael D. Popitz, where the pillow features a plurality of strategically placed recesses designed to place a side-sleeper's head and neck in a lateral sniff position in which the lower cervical spine is in maximal forward flexion, the upper cervical spine is in substantially maximal extension, and the mouth is open. The intention of the patented pillow is to use this position to maximize the airway passage between the mouth and larynx.

However, the lateral sniff position is not a naturally comfortable one, whereby the unnatural feel and discomfort may be detrimental to the user's ability to fall asleep. In addition, while the prior patent contemplates inclusion of two differently oriented head recesses in the pillow to allow the user to choose whether to sleep on their left or right side, the patent doesn't give consideration to relative positioning of a couple sharing the same bed and both wishing to use the patented pillow.

Accordingly, there remains room for improvements and alternatives in pillows intended to treat airway related conditions such as sleep apnea and snoring.

SUMMARY OF THE INVENTION

According to a first aspect of the invention, there is provided an apparatus for treating snoring and/or sleep apnea, said apparatus comprising a pillow having:
  a front surface;
  a rear surface opposite the front surface;
  a left side surface;
  a right side surface opposite the left side surface;
  a bottom surface;
  a top surface opposite the bottom surface;
  a head recess formed in the top surface, the head recess comprising:
    a bottom area for receiving and supporting a lateral side of a user's face, and
    a peripheral area spanning upwardly to the top surface of the pillow from the bottom area of the head recess at a perimeter thereof;
  a neck channel recessed in the top surface and extending from the head recess toward the front surface of the pillow to receive and support a lateral side of a user's neck;
  wherein the peripheral area of the head recess includes a chin region reaching laterally outward from the neck channel at a relative angle thereto toward one of the left and right side surfaces of the pillow for receipt of an underside of the user's chin against said chin region, said chin region being suitably oriented relative to the neck channel such that a user's upper cervical spine resides in a substantially or fully relaxed non-extended state and a user's mandible is maintained in a substantially or fully closed position.

According to a second aspect of the invention, there is provided a sleep apparatus comprising at least one pillow, each comprising:
  a front surface;
  a rear surface opposite the front surface;
  a left side surface;
  a right side surface opposite the left side surface;
  a bottom surface;
  a top surface opposite the bottom surface;
  a first head recess formed in the top surface, and a first neck channel recessed in the top surface and extending from the first head recess toward the front surface of the pillow;
  a second head recess formed in the top surface, and a second neck channel recessed in the top surface and extending from the second head recess toward the front surface of the pillow;
  a third head recess formed in the bottom surface, and a third neck channel recessed in the bottom surface and extending from the third head recess toward one of either the front surface or rear surface of the pillow; and
  a fourth head recess formed in the bottom surface, and a fourth neck channel recessed in the bottom surface and extending from the fourth head recess toward said one of either the front surface or rear surface of the pillow;
  wherein the first and second head recesses in the top surface face inwardly toward one another, and the third and fourth head recesses in the bottom surface face outwardly away from one another.

The pillow may feature a multi-layer construction comprising a top piece having a first pair of head-shaped cutouts therein forming peripheral areas of the first and second head recess, a bottom piece having a second pair of head-shaped cutouts therein forming peripheral areas of the third and fourth head recesses, and a middle piece sandwiched between the top and bottom pieces.

The pillow may be manufactured by cutting the head-shaped cutouts in the top and bottom pieces, and bonding the middle piece between the top and bottom pieces.

According to a third aspect of the invention, there is provided a sleep system for use by a couple, said system comprising:
  first and second pillows, each comprising:
    a front surface;
    a rear surface opposite the front surface;
    a left side surface;
    a right side surface opposite the left side surface;
    a bottom surface; and
    a top surface opposite the bottom surface;
  wherein the first pillow comprises:
    a first head recess formed in the top surface of the first pillow, and a first neck channel recessed in said top surface of the first pillow and extending from the first head recess toward the front surface of the first pillow; and
    a second head recess formed in the top surface of the first pillow, and a second neck channel recessed in the top surface of the first pillow and extending from the second head recess toward the front surface of the first pillow;
  and the second pillow comprises:
    a third head recess formed in the top surface of the second pillow, and a third neck channel recessed in the top surface of the second pillow and extending from the third head recess toward the front surface of the second pillow; and a fourth head recess formed in the top surface of the second pillow, and a fourth neck channel recessed in the top surface of the second pillow and extending from the fourth head recess toward said the front surface of the second pillow;

wherein the first and second head recesses in the top surface of the first pillow face inwardly toward one another, and the third and fourth head recesses in the top surface of the second pillow face outwardly away from one another.

The first and second pillows may each features a multi-layer construction comprising a first piece having head-shaped cutouts therein forming peripheral areas of the head recesses of said pillow, and an underlying second piece beneath the first piece and defining bottom areas of the head recesses of said pillow.

According to a fourth aspect of the invention, there is provided a method of manufacturing a pillow having at least one head recess therein, said method comprising cutting at least one head-shaped cutout in a first piece, and bonding a second piece to said first piece in a position underlying the at least one head-shaped cutout therein, whereby the head-shaped cutout defines a peripheral area of the head recess and the second piece defines a bottom floor area of said head recess.

The method may include cutting at least one additional head-shaped cutout in a third piece, and bonding said third piece to the second piece on a side thereof opposite the first piece.

BRIEF DESCRIPTION OF THE DRAWINGS

Preferred embodiments of the invention will now be described in conjunction with the accompanying drawings in which.

DETAILED DESCRIPTION

Figure 1:
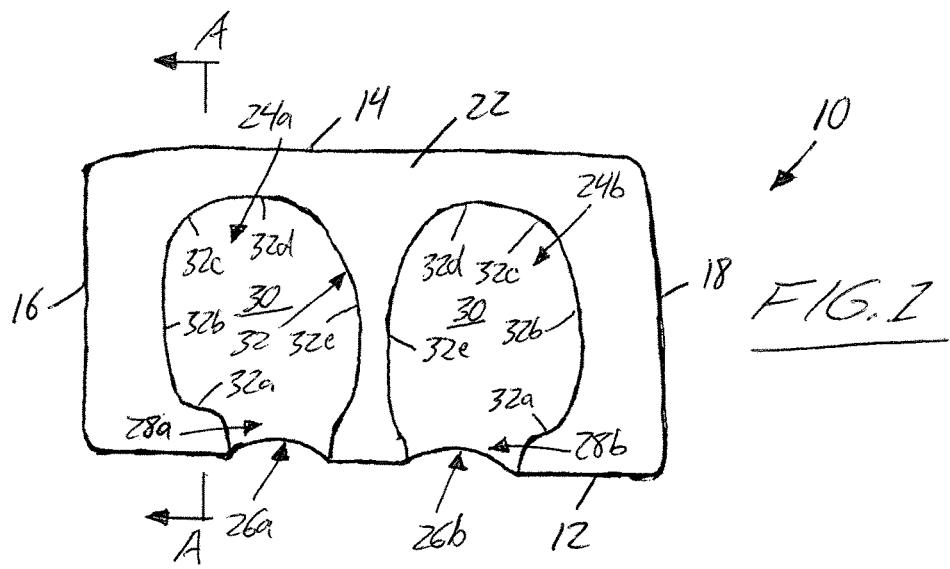
FIG. 1 is an overhead plan view of a single-sided anti-snoring and sleep apnea pillow according to a first embodiment of the present invention.
Figure 2:
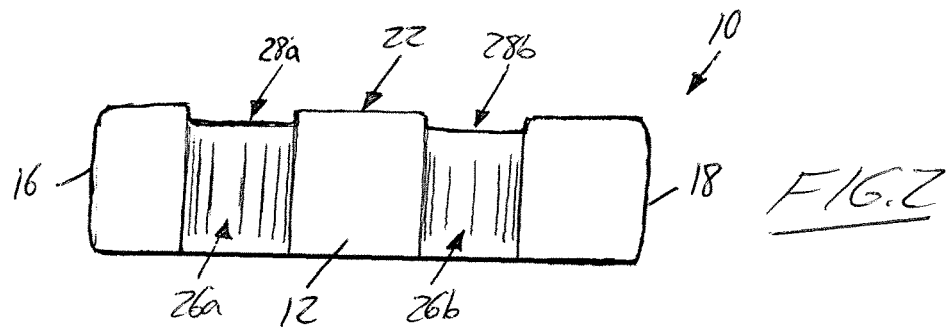
FIG. 2 is a front elevational view of the pillow of FIG. 1.
Figure 3:
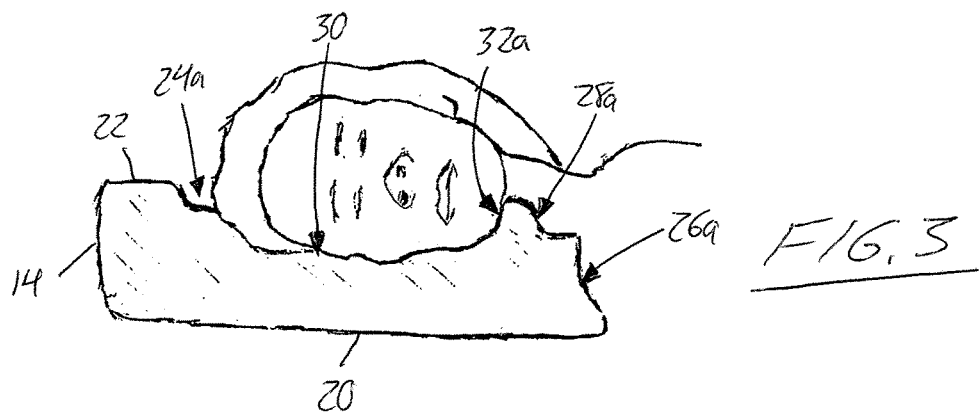
FIG. 3 is a cross-sectional view of the pillow of FIG. 1, as taken along line A-A thereof, while in use.

FIGS. 1 through 3 illustrates a single-sided, dual-position, anti-snoring and sleep apnea pillow according to a first embodiment of the present invention. The pillow 10 comprises a body of resiliently compressible material, such as a viscoelastic polyurethane foam material (memory foam), having a front surface 12, an opposing and parallel rear surface 14, a left side surface 16, an opposing and parallel right side surface 18, a bottom surface 20 and an opposing and parallel top surface 22. The left and right side surfaces perpendicularly interconnect the front and rear surfaces at opposing ends thereof, and these four surfaces are oriented in vertically upright planes and denote four perimeter sides of the pillow, which therefore has a generally rectangular outer shape in the illustrated example, though the shape may be varied and need not necessarily have flat, planar surfaces on all perimeter sides thereof.

The bottom surface resides in a horizontal plane from which the perimeter sides reach upwardly around the perimeter of the bottom surface and join with the perimeter of the opposing top surface. In the illustrated embodiment, the top surface is parallel to the bottom surface, meaning that a thickness of the pillow between the top and bottom surfaces is uniform around the full perimeter of the pillow. On the other hand, in other embodiments, the upper surface may be sloped in one or more directions, for example in the manner disclosed in the aforementioned patent, the entirety of which is incorporated herein by reference.

The pillow 10 features two headrest zones each designed to accommodate receipt of the head and neck of a user lying in a lateral decubitus position (on their side). The two headrest zones are of identical configuration to one another, but of mirrored relation to one another across a central mid-plane $P_M$ of the pillow that vertically bisects the front and rear surfaces thereof, whereby the user can select between the two available headrest zones depending on whether they want lie one their left or right side.

A first headrest zone thus features a first head recess 24a recessed into the top surface 22, a first shoulder recess 26a concavely recessed into the front surface 12, and a first neck channel 28a recessed into the top surface 22 and spanning from the first head recess 24a to the first shoulder recess 26a. In the illustrated embodiment, each head recess is flat-bottomed, thus having a flat bottom area 30 of shape generally resembling a human facial profile. A peripheral wall area 32 stands vertically upright from the flat bottom area 30 of each recess around a perimeter thereof.

The peripheral wall area 32 thus follows the facial profile path around the perimeter of the bottom area 30 of the head recess, and therefore includes a chin region 32a that reaches laterally outward from a respective side of the neck channel 28a toward the nearest side of the pillow. The first head recess 24a resides nearer to the left side surface 16 of the pillow than the right side surface 18 thereof, whereby the chin region 32a of the peripheral wall area 32 of the first head recess 24a reaches laterally outward from the left side of the first neck channel 28a in a leftward direction toward the left side surface 16 of the pillow. The chin region transitions concavely into a facial region 32b of the peripheral wall area that then spans toward the rear surface 14 of the pillow at a distance inward from the left side surface 16 thereof. Nearer to the rear surface 14 of the pillow, a forehead region 32c of the peripheral wall transitions concavely from the facial region 32b to an upper head region 32d that spans along the rear surface 14 of the pillow toward the right side surface 18 thereof furthest from the first head recess 24a, before concavely transitioning into a crown and nape region 32e that then spans forwardly back toward the front surface 12 of the pillow to join up with the right side of the first neck channel 28a.

The second headrest zone is of identical configuration but mirrored orientation to the first headrest zone. Accordingly, the second headrest zone thus features a second head recess 24b recessed into the top surface 22 of the pillow, a second shoulder recess 26b concavely recessed into the front surface 12 of the pillow, and a second neck channel 28b recessed into the top surface 22 of the pillow and spanning from the second head recess 24b to the second shoulder recess 26b. The different regions of the peripheral wall area 32 of the second head recess 24b are the same as described above for the first head recess 24a, except that due to the mirrored relationship between the two head recesses, the chin region 32a of the peripheral wall area 32 of the second head, recess 24b reaches laterally outward from the right side of the second neck channel 28b in a rightward direction toward the right side surface 18 nearest the second head recess, the upper head region 32d spans leftward toward the left side surface 16 furthest from the second head recess 24b, and the crown and nape region 32e joins up with the left side of the second neck channel 28b.

A user can lay their head in the first head recess 24a if they wish to sleep on their right side and face the left side 16 of the pillow, or can lay their head in the second head recess 24b if they wish to sleep on their left side and face the right side 18 of the pillow. In either position, the shoulder on which the user is laying tucks into the respective shoulder recess 26a, 26b joined to the selected head recess 24a, 24b, and the lateral side of the user's neck is laid in and supported by the neck channel 28a, 28b that provides this interconnection of the selected head recess and respective shoulder recess.

Figure 14:
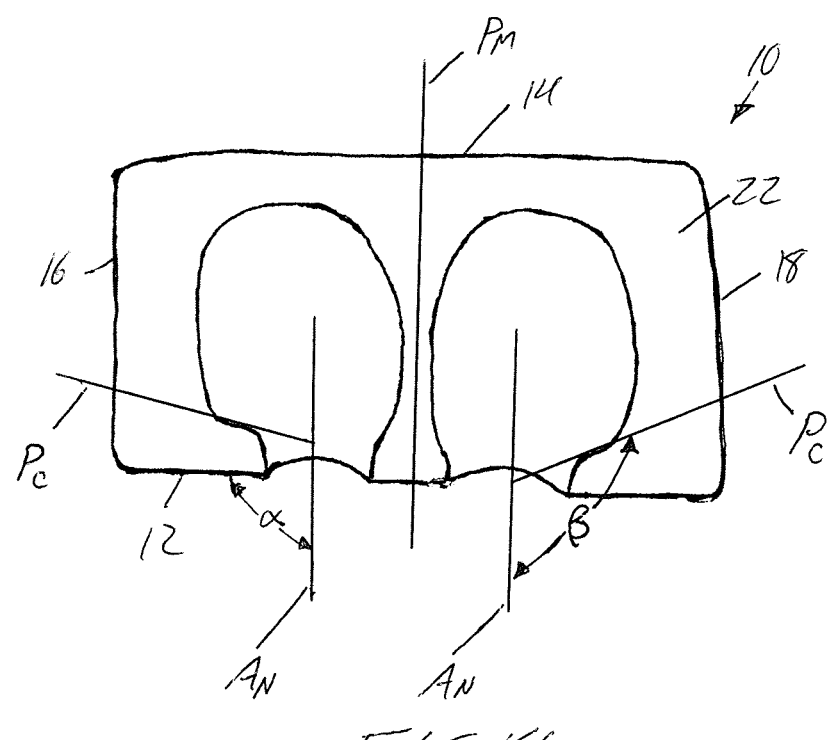
FIG. 14 is a schematic overhead plan view illustrating a headrest geometry employed in the pillow of each embodiment.

With reference to the geometric markup in FIG. 14, a neck channel axis $A_N$ of each neck channel 28, 28b defines the direction in which the neck channel reaches from the respective shoulder recess at the front surface 12 into the respective head recess. This neck channel axis $A_N$ resides at a first angle $\alpha$ to the front surface 12 of the pillow, the measure of which is preferably between 80 and 100-degrees, more preferably between 85 and 95 degrees in some embodiments, and is approximately 90-degrees in one particular embodiment. This relative orientation of the neck channel relative to the shoulder recess at the front of the pillow denotes a relatively relaxed, natural position of the user's neck with zero or minimal flexion and extension. A reference plane $P_C$ denoting a direction in which the chin segment 32a of the peripheral wall area angles outwardly from the respective side of the neck channel lies at a second angle $\beta$ relative to the neck channel axis $A_N$. The measure of angle $\beta$ is preferably between 80 and 120-degrees, more particularly between 80 and 110-degrees in some embodiments, even more particularly between 85 and 100 degrees in some embodiments, and is approximately 90-degrees in one particular embodiment.

This relative orientation of the chin segment means that receipt of the user's chin against the chin segment 32a of the peripheral wall area 32 of the selected head recess acts to place or the user's mandible into a fully or substantially closed position to help keep the user's mouth closed when sleeping. This is best shown in FIG. 3, where the underside of the user's chin is abutted against chin segment 32a of the peripheral wall area of the first head recess, while the lateral side of the user's face rests on the bottom 30 of the head recess. As shown, the resilient compressibility of the pillow body material may allow some conforming deformation of the normally-flat bottom area 30 of the head recess under the weight of the user's head, provided that the material is still sufficiently stiff at the area between the chin segment 32a and the front surface of the pillow 12 in order to effectively resist attempted opening of the user's mouth during sleep.

In testing prototypes of the invention, Applicant has found that maintaining the roughly ninety-degree or right-angle relationship between the neck and chin while also maintaining the closed mouth position of the lower jaw helps to reduce or avoid both sleep apnea airway obstruction events and snoring, all while avoiding an unnatural and uncomfortable flexion and extension of neck to thereby allow the user to fall asleep with relative ease.

In the illustrated embodiments, both the head recess and the connected neck channel are flat-bottomed, and the planar bottom areas thereof are coplanar with one another. However, in other embodiments, the bottom area of the head recess, neck channel or both may depart from a purely planar form, in which case some areas of the head recess may have a gradual slope from the bottom thereof to the top surface of the pillow rather than a steeply vertical peripheral wall, and so the term peripheral area is used to define outer regions of the head recess where it joins up with the top surface of the pillow, regardless of whether this is a steep vertical wall or a more gradually sloped area. However, sufficient steepness or vertically should be ensured specifically at the chin segment 32a of the peripheral area to ensure this chin segment 32a effectively hooks under the chin to place and hold the mandible in the closed position. To ensure sufficient contact area with the chin, the depth of the head recess from the top surface of the pillow to the bottom area of the head recess at the chin segment is preferably at least 1-inch, for example measuring between 2-inches and 3-inches in some embodiments, and being approximately 2.5 inches in one particular embodiment. Also, instead of the bottoms of the head recess and neck channel being flush with one another, the bottom of the neck channel may alternatively be elevated relative to the bottom of the head recess, for example as disclosed in the prior patent incorporated herein.

While the forgoing embodiment has head recesses oriented in outward facing positions in which their facial segments face outwardly away from one another, i.e. with the facial segment of each head recess facing outwardly toward the nearest side surface of the pillow, the two head recesses may alternatively be oriented in inward facing positions in which their facial segments face toward one another, i.e. with the facial segment of each head recess facing inwardly past the mid-plane $P_M$ toward furthest side of the pillow. Either way, the user can use the pillow by selecting from the two headrest zones based on whether they want to sleep on their left or right side. However, the single-sided nature of the first embodiment pillow has limitations on the relative sleeping positions attainable by a couple who are both using a respective first embodiment pillow 10.

Figure 4:
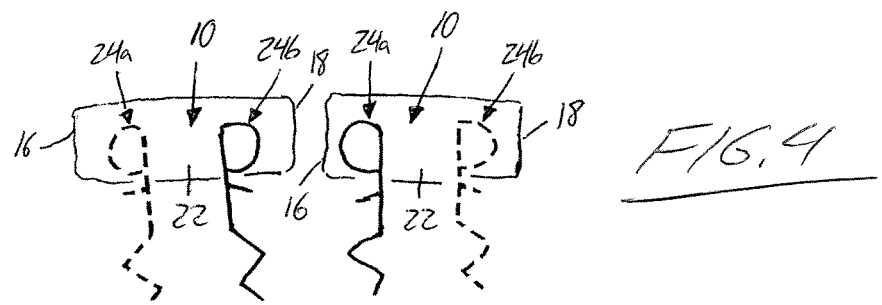
FIG. 4 is a schematic overhead plan view illustrating side-by-side use of a pair of the first embodiment pillows by a couple, and showing different sleeping positions attainable by said couple during such use.

This is demonstrated by FIG. 4, where two first embodiment pillows 10 are placed side by side for respective use by the two individuals sharing the same bed, but each having their own pillow. If the couple wish to sleep in close proximity to one another, then the user on the left side of the bed selects the right headrest zone of their pillow, and the user on the right side of the bed selects the left headrest zone of their pillow. In other words, each user selects the headrest zone at the side of their pillow that neighbours the other pillow.

However, in the outward-facing configuration of the illustrated first embodiment, this means that the couple can only lie in a face-to-face position with one another at the neighbouring sides of the pillows, and cannot attain a spooning position in which one individual faces the rear of the other. If both pillows had an inward facing headrest zones, the same problem would remain, in that a back-to-back position would be the only possibility at the neighbouring sides of the two pillows, and a spooning position is once again unattainable. Broken lines show how the users may choose to sleep further apart from one another by occupying the headrest zones at non-neighbouring sides of the two pillows nearest the sides of the bed. So while the first embodiment gives flexibility in terms of left-side and right-side sleeping options for each user, and the degree of relative spacing between the two users, it makes intimate spooning impossible for two users of identical one-sided pillows.

Figure 5:
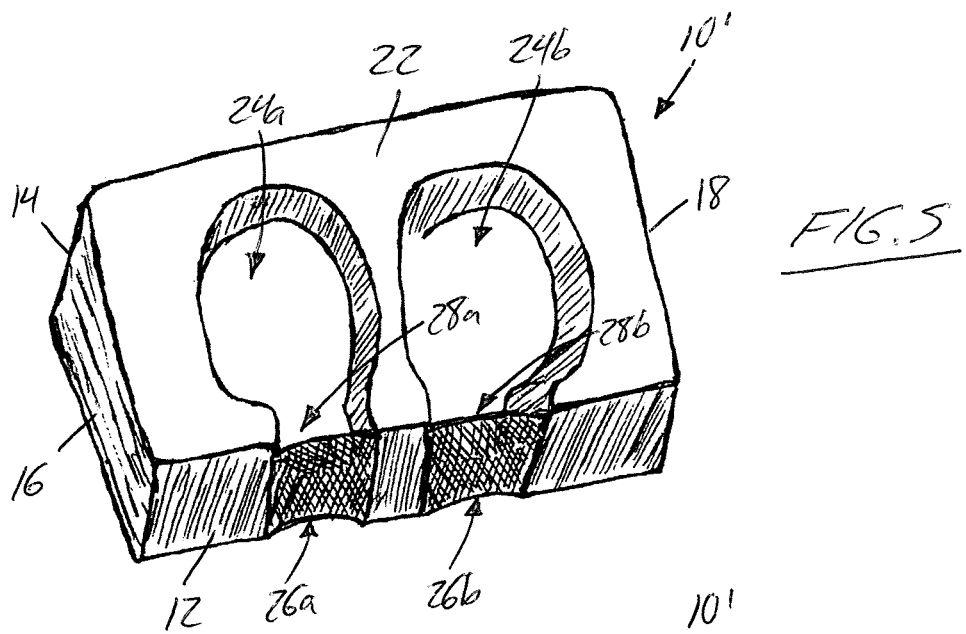
FIG. 5 is a top perspective view of a double-sided anti-snoring and sleep apnea pillow according to a second embodiment of the present invention.
Figure 6:
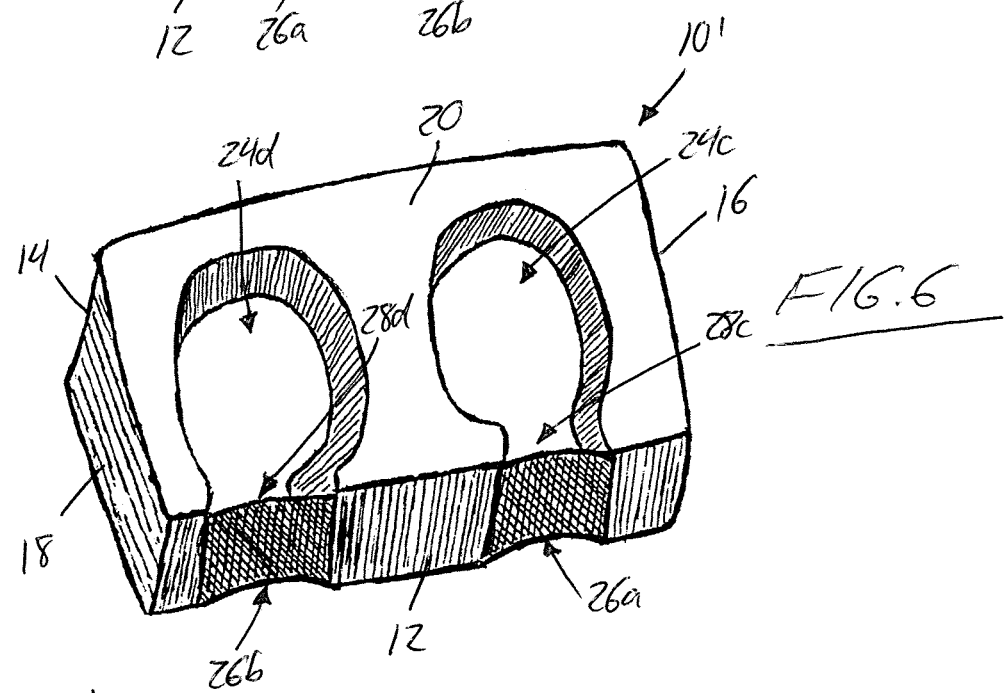
FIG. 6 is a bottom perspective view of the pillow of FIG. 5.
Figure 7:
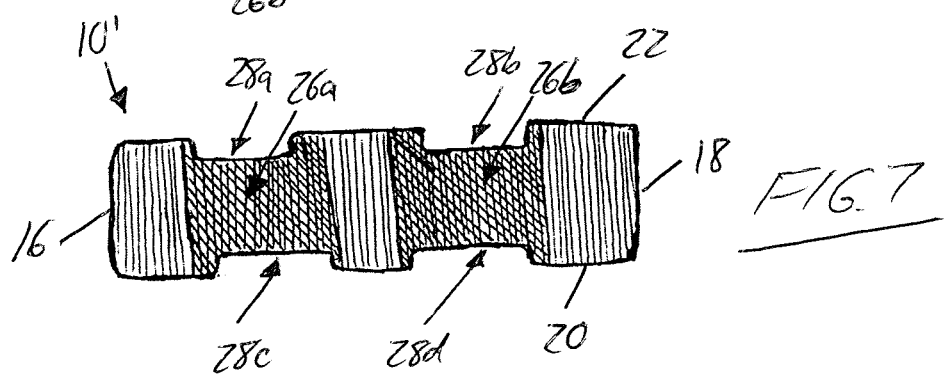
FIG. 7 is a front elevational view of the pillow of FIG. 5.

FIGS. 5 to 7 illustrate a second embodiment pillow 10' that overcomes this shortcoming of the first embodiment. The second embodiment has the same two headrest zones as the first embodiment, thus having first and second head recesses 24a, 24b and neck channels 28a, 28b recessed in the top surface, but also has two additional headrest zones recessed in the bottom surface 20 of the pillow. So with reference to FIG. 6, which shows the second embodiment pillow 10' in an inverted position with the bottom surface 20 facing upward, a third head recess 24c, a third neck channel 28c, fourth head recess 24d and a fourth neck channel 28d are all recessed in the bottom surface 20 of the pillow 10'.

The third head recess 24c and third neck channel 28c respectively underlie the first head recess 24a and first neck channel 28a in the top surface 22, while the fourth head recess 24d and fourth neck channel 28d respectively underlie the second head recess 24b and second neck channel 28b in the top surface 22. Whereas the first and second head recesses 24a, 24b are in the outward facing configuration where their respective facial and chin segments face and reach outwardly away from one another toward the nearest side surfaces of the pillow, the third and fourth head recesses 24c, 24d are in the inward facing configuration where their respective facial and chin segments face and reach inwardly toward one another. Thus, the chin segment 32a of the third head recess 24c reaches toward the right side surface 18 of the pillow (which is shown on the left in FIG. 6 due to the inverted position of the pillow), while the chin segment 32a of the fourth head recess 24d reaches toward the left side surface 16 of the pillow (which is shown on the right in FIG. 6 due to the inverted position of the pillow).

The second embodiment pillow is thus double-sided, in the sense that it has a headrest zones on both the top and bottom of the pillow. The first shoulder recess 26a is intersected by the first and third neck channels 28a, 28c, and the second shoulder recess 26b is intersected by the second and fourth neck channels 28b, 28d. The first and third headrest zones thus share the first shoulder recess 26a, while the second and fourth headrest zones share the second shoulder recess 26b.

FIG. 8 illustrates use of two of these double-sided second embodiment pillows 10' to enable the users to achieve two different possible spooning positions.

Figure 8A:
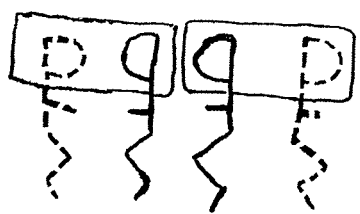
FIGS. 8A and 8B are a schematic overhead plan views illustrating side-by-side use of a pair of the second embodiment pillows by a couple, and showing different sleeping positions attainable by said couple during such use, including spooning positions unattainable in the first embodiment.

FIG. 8A shows the two pillows 10' placed side by the side with the left pillow placed bottom-surface-up, and the right pillow placed top-surface-up, whereby the third headrest zone of the left pillow and the first headrest zone of the right pillow reside adjacent the neighbouring sides of the two pillows and are therefore usable to enable the sleeping couple (shown in solid lines) to occupy a left-facing spooning position. That is, the user of left pillow makes use of third headrest zone of that pillow by laying their head and neck in the third head recess 24c and third neck channel 28c, and the user of right pillow makes use of first headrest zone of that pillow by laying their head and neck in the first head recess 24a and first neck channel 28a.

Figure 8B:
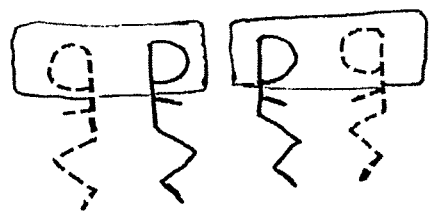

FIG. 8B shows the two pillows 10' placed side by the side with the left pillow placed top-surface-up, and the right pillow placed bottom-surface-up, whereby the second headrest zone of the left pillow and the fourth headrest zone of the right pillow reside adjacent the neighbouring sides of the two pillows and are therefore usable to enable the sleeping couple (shown in solid lines) to occupy a right-facing spooning position. That is, the user of left pillow makes use of second headrest zone of that pillow by laying their head and neck in the second head recess 24b and second neck channel 28b, and the user of right pillow makes use of fourth headrest zone of that pillow by laying their head and neck in the fourth head recess 24d and fourth neck channel 28d. Alternatively, as shown in dotted lines, the user of either pillow may move to the other available headrest zone of the upward facing surface of the respective pillow to allow the couple of occupy other positions of varying distance and orientation to one another.

While the illustrated embodiment of FIGS. 5 to 7 has two shoulder recesses 26a, 26b shared by the four headrest zones at the front surface 12 of the pillow, it will be appreciated that the inward facing third and fourth headrest zones may alternatively be oriented such that their neck channels 28c, 28d intersect the rear surface 14 of the pillow instead of the front surface 12, in which case third and fourth shoulder recesses would be provided at the rear surface 14 of the pillow for intersection thereof by the third and fourth neck channels 28c, 28d. Whereas the illustrated embodiment requires mere flipping of the pillow between right-side-up and inverted positions to switch from the first and second headrest zones to the third and fourth headrest zones, the variant with the third and fourth headrest oriented to intersect the rear surface of the pillow would require both flipping over of the pillow, and rotation thereof through 180-degrees.

Figure 9:
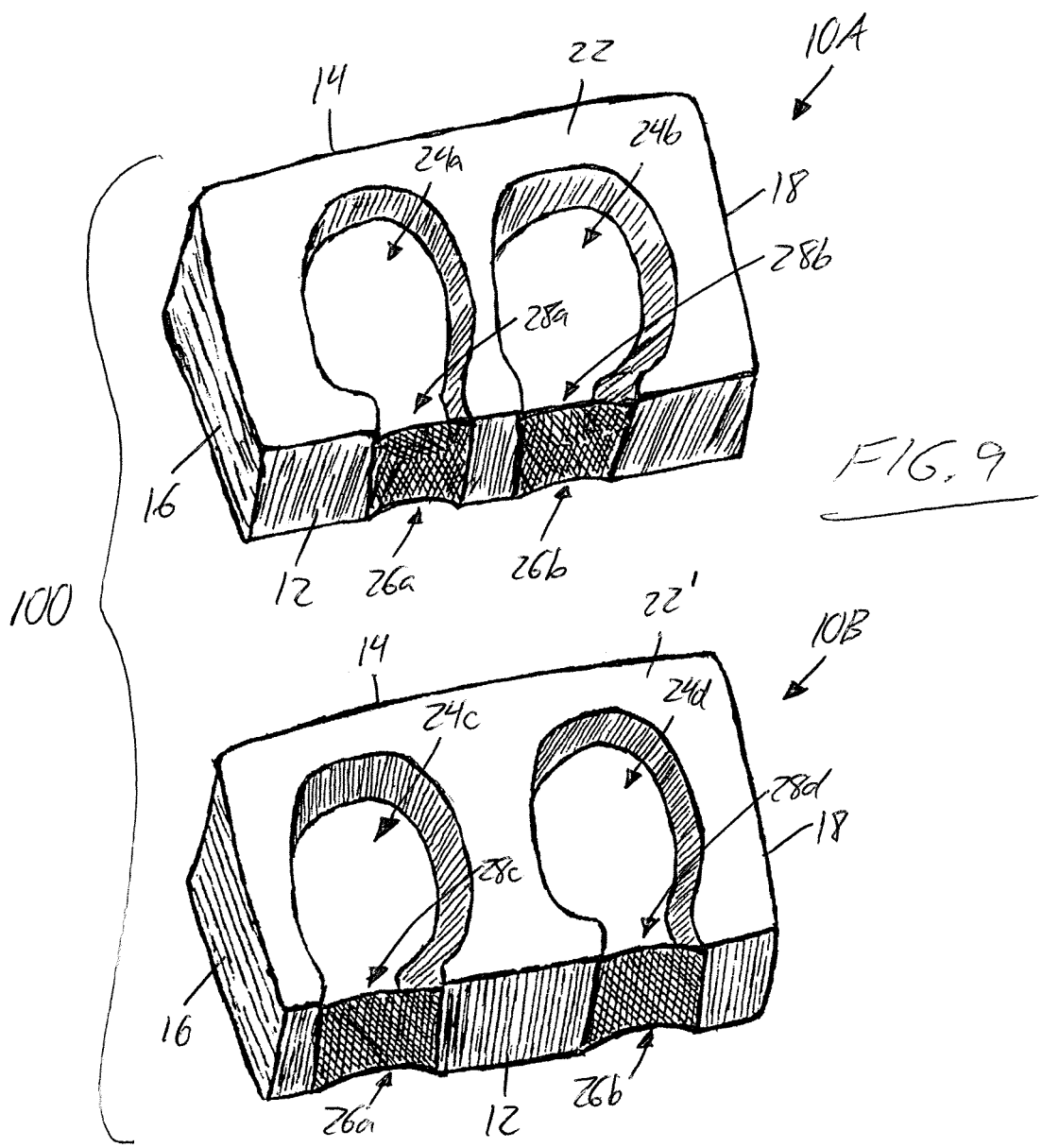
FIG. 9 illustrates a two-pillow set according to a third embodiment of the present invention in which two single-sided pillows are usable side-by-side to attain the aforementioned spooning positions.

FIG. 9 illustrates a two-pillow set 100 according to a third embodiment of the invention that enables the same spooning position options as the second embodiment, but uses two differently configured single-sided pillows to do this. Here, the top surface 22 of a first pillow 10A of the set has the same first and second outwardly-facing headrest zones described for the first embodiment pillow and used in the top surface of the second embodiment pillow. Meanwhile, the top surface 22' of a second pillow 10B of the set has the same third and fourth inwardly-facing headrest zones used in the lower surface of the second embodiment pillow. The bottom surface of both pillows may be a flat surface lacking any headrest zones. The two pillows of the set can be placed side by side with the first pillow 10A on the right and the second pillow 10B on the left to accomplish the left-facing spooning position of FIG. 8A, or with the first pillow 10A on the left and the second pillow 10B on the right to accomplish the right-facing spooning position of FIG. 8B.

Figure 10:
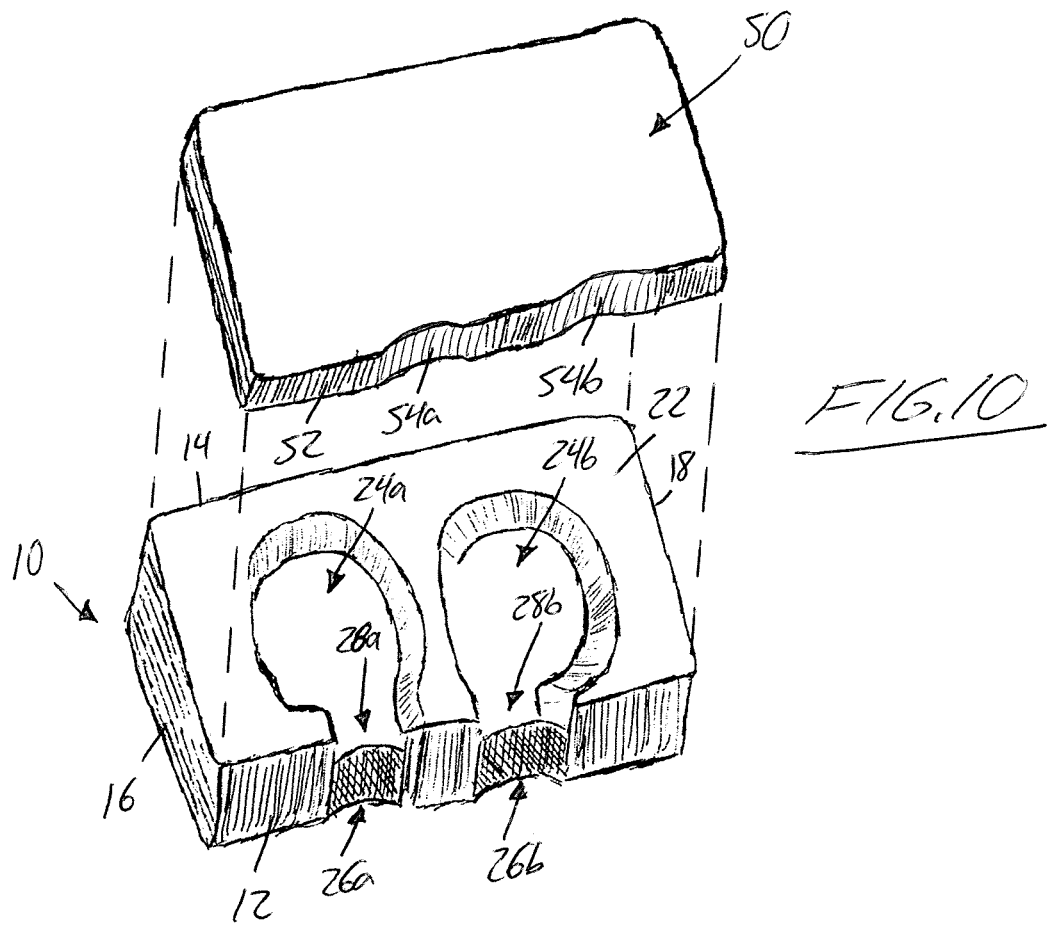
FIG. 10 illustrates optional addition of a pillow topper for the pillow of any of the forgoing embodiments.

FIG. 10 is an exploded view illustrating optional inclusion of a pillow topper 50 to accompany each pillow of any preceding embodiment. The pillow topper is also made of a body of resiliently compressible material, such as a viscoelastic polyurethane foam material (memory foam), but has a lesser thickness than the pillow, and also has a lesser compressibility than the pillow in order to act as more shape-conforming pad for placement atop the less compressible pillow body to improve the comfort thereof during use. In one non-limiting example, the pillow topper may have a thickness of 2-inches, relative to a pillow thickness of 4-inches measured between the top and bottom surface of the pillow.

The pillow topper 50 has a suitable size and shape to fully cover at least the two head recesses in the top or bottom surface of the pillow when placed thereon. In the illustrated example, an outer perimeter of the pillow topper is of equal measure to that of the pillow so that the pillow topper 50 covers an entirety of the top or bottom surface of the pillow when placed in an aligned position thereon. The user lays their head and neck atop the pillow topper 50 at a position thereon overlying the head recess and neck channel of the selected headrest zone of the pillow, whereby under the weight of the user's head and neck, the topper 50 is depressed into the head recess and neck channel. Due to the compressibility and reduced thickness of the pillow topper, it substantially conforms to the shape of the head recess and neck channel of the firmer pillow to provide additional padding on the bottom areas of the head recess and neck channel to improve user comfort. In the version shown in FIG. 10, the front surface 52 of the pillow topper has two additional shoulder recesses 54a, 54b therein of matching shape and position to the first and second shoulder recesses of the pillow.

Figure 11:
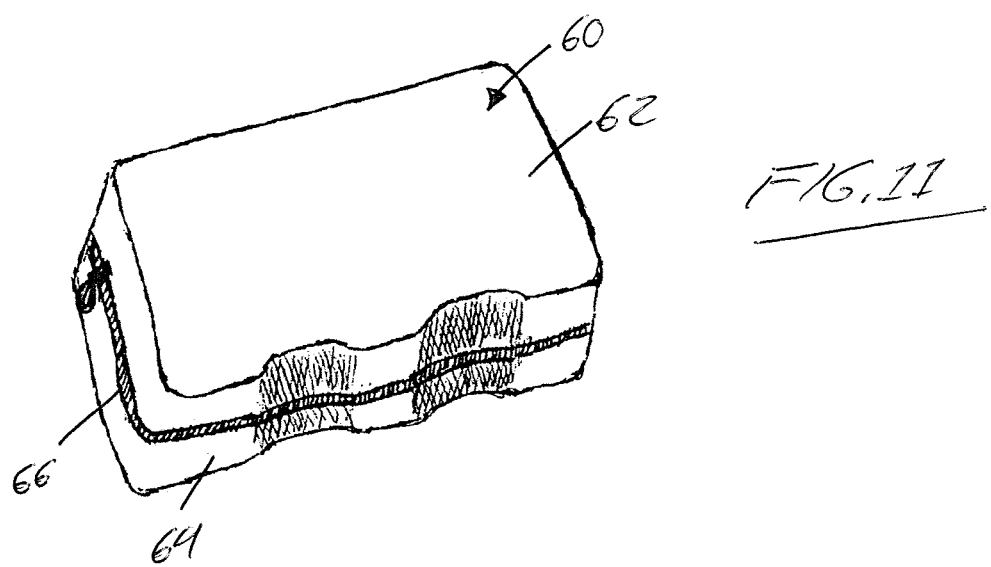
FIG. 11 illustrates addition of a zipper cover for containing the pillow and pillow topper of FIG. 10.

FIG. 11 shows additional inclusion of a zippered cover 60 having two clamshell-like halves 62, 64 formed of fabric or other flexible material. The two halves cooperatively define a hollow interior space of sufficient size to accommodate both the pillow 10 and the pillow topper 50 placed thereon. A zippered closer 66 spans across a front side of the cover that overlies the front surfaces of the pillow and topper inside. The zippered closure 66 also spans a full or majority length of left and right sides of the cover that overlie the left and right side surfaces of the pillow and topper inside.

The zippered closure 66 preferably has its two terminal ends disposed on the sides of the cover 60 so that these ends of the zipper closure, and the zipper pull tab when closed, don't create discomfort for the user whose shoulders and torso lie at the front side of the cover during use of the covered pillow and topper. The zipper closure may alternatively span a portion of the rear side of the cover, thus placing the terminal ends of the zippered closure at the rear side, thereby still leaving the front side of the cover free of the zipper's terminal features and pull tab for optimal comfort. That being said, inclusion of the zipper closure 66 on only three of the cover's four sides enables sufficient opening of the cover to allow insertion and removal of the pillow and topper, for example to enable washing of the empty cover separately of the pillow and topper. In another embodiment, the zippered closure 66 may span only the rear and left and ride sides of the cover, and leave the front side of the cover entirely free of any zipper components.

Figure 12:
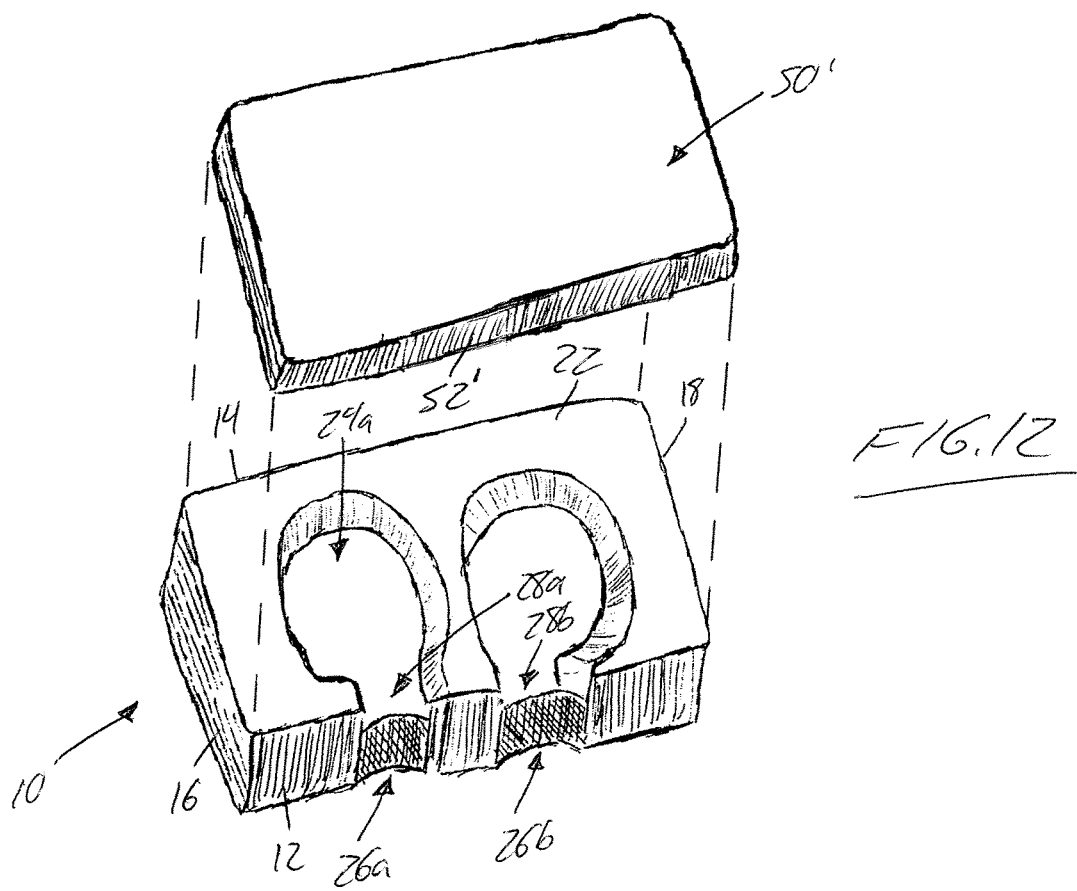
FIG. 12 illustrates one possible variation in the shape of the pillow topper.

FIG. 12 shows a variation on the topper 50' which lacks any shoulder recesses therein, and thus has a purely rectangular perimeter with a fully flat or linear front surface 52'. Here, the front surface 52' that overlies the selected shoulder recess of the pillow 10 can be pushed down by the user's neck weight into a position overlying the corner edge where the bottom of the neck channel intersects the shoulder recess, thereby improving neck and shoulder comfort for the user.

Figure 13:
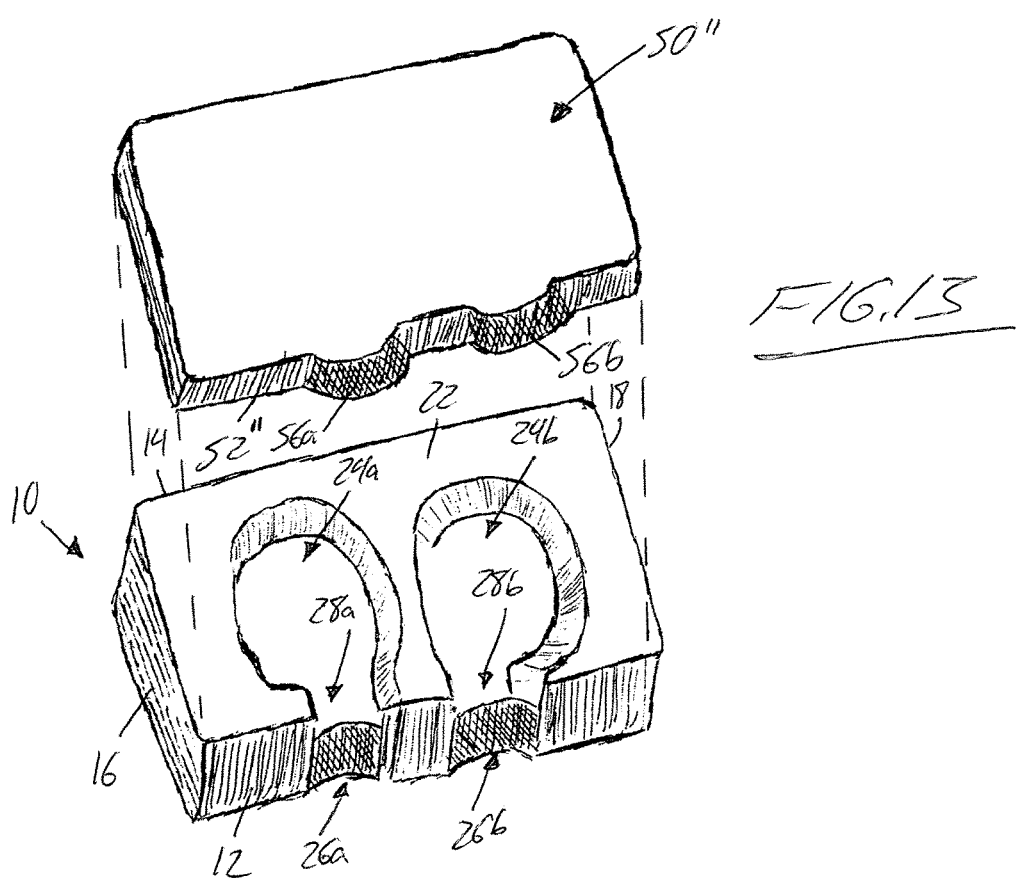
FIG. 13 illustrates another possible variation in the shape of the pillow topper.

FIG. 13 shows another variation on the topper 50" where instead of shoulder recesses, the front surface 52" of the topper features two tab-like protrusions 56a, 56b that bulge outwardly from the remainder of the otherwise flat or linear front surface 52" at locations overlying the shoulder recesses 26a, 26b of the pillow, thereby increasing the amount of topper material available for downward folding over the neck/shoulder corner edge of the pillow under the weight of the user's neck in order to further line this neck/shoulder space of the pillow with the more compressible topper material for maximum neck/shoulder comfort.

While the illustrated embodiments of the topper feature flat and parallel top and bottom surfaces separated by a uniform thickness of the topper, and also feature straight front, rear, left and right sides (except for the optional inclusion of the additional shoulder recesses 54a, 54b or protrusions 56a, 56b), the particular shape of the topper may be varied without departure from the described purpose and functionality.

While the illustrated embodiment shows only a single topper, a second topper may be included for placement over the third and fourth head recesses in the bottom surface of the second embodiment pillow, in which case the cover is provided with a large enough interior to accommodate the pillow and both of the toppers. This way, the double-sided pillow can be used comfortably in either the top-surface-up or bottom-surface-up orientation without having to open up the cover to relocate the topper from one side of the pillow to the other. The second topper may be identical to the first.

Figure 15:
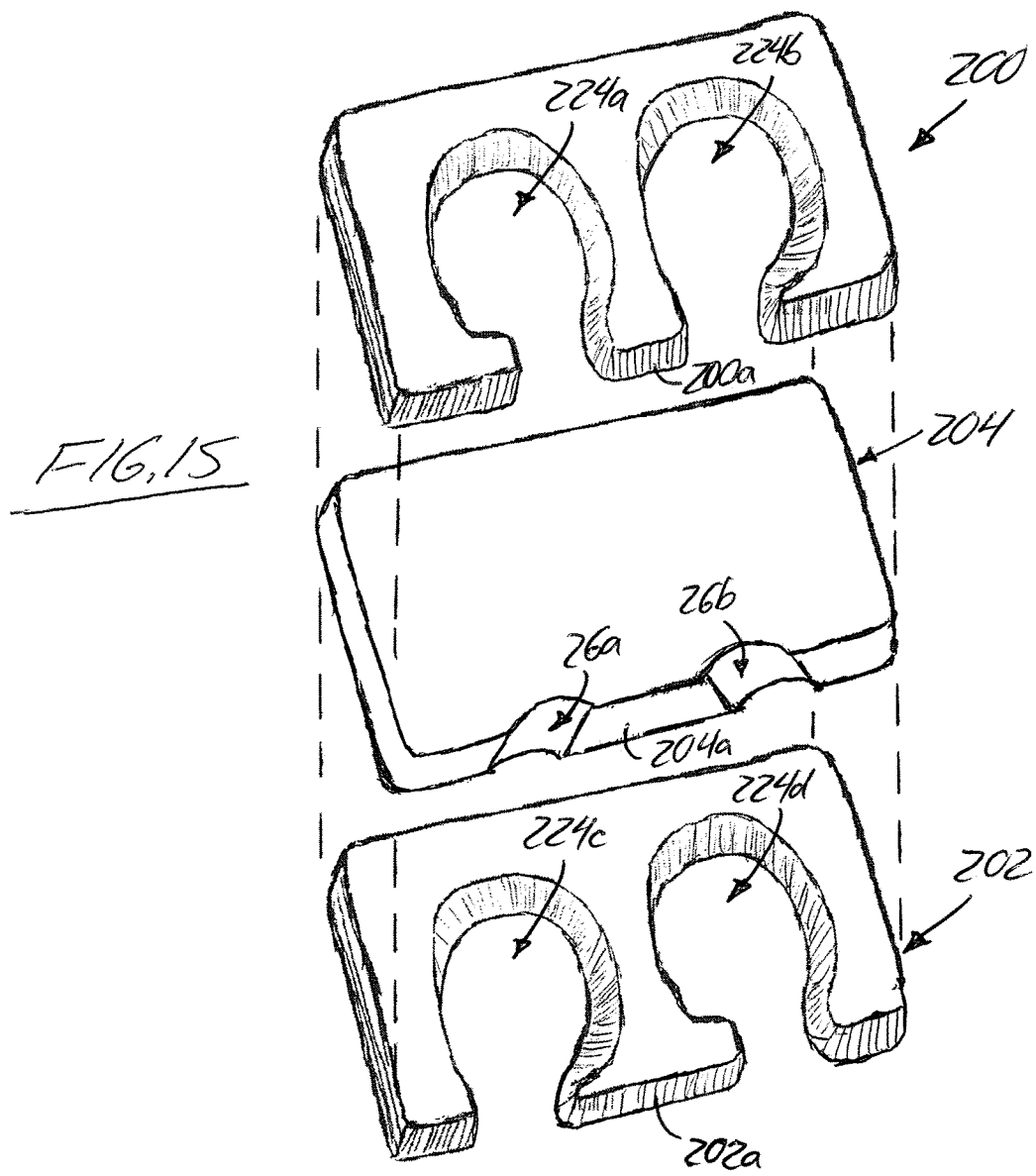
FIG. 15 is an exploded top perspective view of a fourth embodiment pillow constructed in layered fashion.
Figure 16:
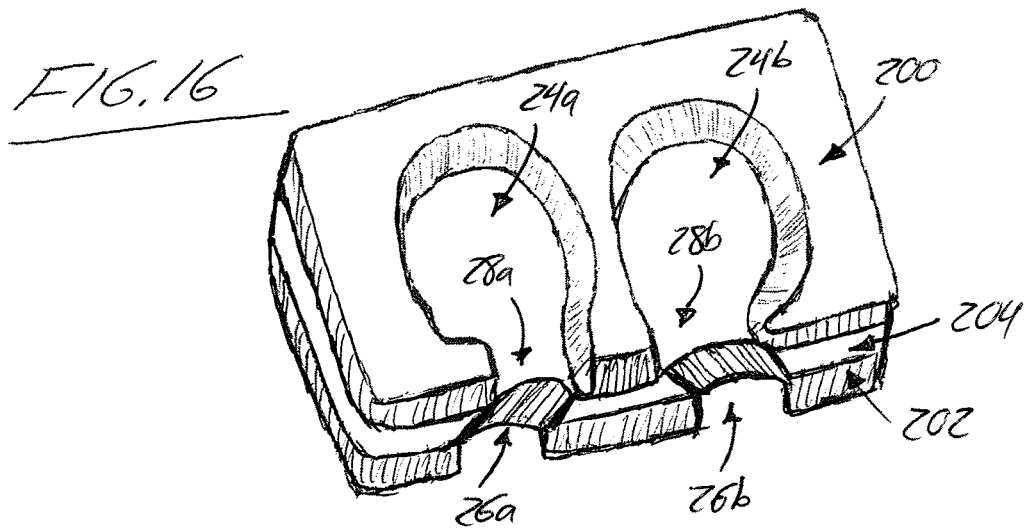
FIG. 16 is a top perspective view of the fourth embodiment pillow of FIG. 15 in a finished state.

FIGS. 15 and 16 illustrate a fourth embodiment, which in its finished state of FIG. 16 has the same overall shape and form as the second embodiment, but as shown in FIG. 15, the body of the pillow features a multi-piece construction rather than the single piece construction of the second embodiment. The illustrated example employs a three-piece construction, with a top piece 200, bottom piece 202 and a middle piece 204 each formed of resiliently compressible material, for example the aforementioned viscoelastic polyurethane foam material (memory foam). The top piece 200 features two head-shaped openings 224a, 224b therein that both pass fully through the top piece 200 in the thickness dimension thereof, from a topside of the top piece that defines the top surface 22 of the finished pillow to an opposing underside of the top piece. The bottom piece 202 likewise features two head-shaped openings 224c, 224d therein that both pass fully through the bottom piece 202 in the thickness dimension thereof, from an underside of the bottom piece that defines the bottom surface 20 of the finished pillow to an opposing topside of the bottom piece. Each head-shaped opening includes a neck portion that intersects a front edge 200a, 202a of the top or bottom piece 200, 202. The head-shaped openings in the top piece face away from one another, while the head-shaped openings in the bottom piece face toward one another.

The middle piece 204 lacks any head-shaped openings therein, but has two shoulder recesses 26a, 26b formed in a front edge 204a of the middle body at positions that align with the neck portions of the head-shaped channels in the top and the bottom pieces. Each piece 200, 202, 204 is of generally rectangular shape and generally equal area to one another in plan view. In the finished state of the pillow, the three pieces are stacked or layered in generally aligned fashion, whereby aligned front edges of the three pieces collectively define the front surface of finished pillow, aligned left side edges of the three pieces collectively define the left side surface of finished pillow, and aligned right side edges of the three pieces collectively define the right side surface of finished pillow. The front edges of the three pieces, where left intact between the shoulder recesses of the middle piece and between the neck portions of the head-shaped openings in the top and bottom pieces, align, and collectively define the front surface of the finished pillow.

After cutting of the head-shaped openings, and optional shoulder recesses if included, the three pieces are stacked or layered together face-to-to-face with the middle piece sandwiched between the top and bottom pieces, and are bonded together, for example using a suitable foam-compatible adhesive, for example applied to the underside of the top piece and the topside of the bottom piece around the head-shaped openings cut therein. As shown in FIG. 16, the overall shape and configuration of the resulting multi-layer pillow matches that of the second embodiment. The first and second head-shaped openings 224a, 224b of the top piece 200 cooperate with the topside of the middle piece 204 to form the first and second head recesses 24a, 24b and first and second neck channels 28a, 28b of the finished pillow, while the third and fourth head-shaped openings 224c, 224d of the bottom piece 204 likewise cooperate with the underside of the middle piece 204 to form the third and fourth head recesses 24a, 24b and third and fourth neck channels 28a, 28b of the finished pillow. The middle piece thus defines the bottom area 30 or floor of each head recess and neck channel, while the top and bottom pieces define the peripheral wall areas of the head recesses and the sides of the neck channels.

The fourth embodiment may be easier and/or more cost efficient to manufacture, as a simple two-dimensional cutting path in horizontal X and Y directions can be used on the top and bottom pieces to cut the head-shaped openings therein, as opposed to a three-dimensional tooling pattern that would require depth control in a vertical Z-direction to create a head recess in a single-piece pillow body like those of the earlier embodiments. While the illustrated example is a three-piece construction used to manufacture a double-sided pillow with headrest zones on both the top and bottom of the pillow, it will be appreciated that a two-piece construction alternatively may be used to produce a single-sided pillow like that of the first embodiment, in which case the bottom piece may simply be omitted, whereupon the middle piece instead becomes a bottom or base piece of the two-piece pillow construction. In such instance, the head recesses in the remaining top piece may face toward or away from one another, whereby by the finished pillow can resemble either of those shown in FIG. 9. Alternatively, the bottom piece may be included, but with a lack of head-shaped openings therein, whereby the finished pillow would again have three layers, but would have head recesses and neck channels only in the top of the pillow.

The multi-piece construction also allows optional use of different foam characteristics among the different layers of the pillow, for example using foams of different compressibility in the piece(s) with the head openings than in the middle or base piece that defines the facial resting bottom area of the head recess. For example, it may be advantageous to use a stiffer less compressible foam for the top and optional bottom pieces to provide improved resistance to a user's jaw movement, while using a softer more compressible foam for the facial resting bottom areas of the head recesses. Like in any of the other embodiments, a topper and compatible cover may be included in with the multi-layer pillow of the fourth embodiment. A single-sided multi-layer pillow may be accompanied by a single topper, while a double-sided multi-layer pillow may be accompanied by one or two toppers.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. An apparatus for treating snoring and/or sleep apnea, said apparatus comprising a pillow having:
   a front surface;
   a rear surface opposite the front surface;
   a left side surface;
   a right side surface opposite the left side surface;
   a bottom surface;
   a top surface opposite the bottom surface;
   a head recess formed in the top surface, the head recess comprising:
      a bottom area for receiving and supporting a lateral side of a user's face, and
      a peripheral area spanning upwardly to the top surface of the pillow from the bottom area of the head recess at a perimeter thereof; and
   a neck channel recessed in the top surface and extending from the head recess toward the front surface of the pillow to receive and support a lateral side of the user's neck;
   wherein the peripheral area of the head recess includes a chin region reaching laterally outward from the neck channel at a relative angle thereto toward one of the left and right side surfaces of the pillow for receipt of an underside of the user's chin against said chin region, said chin region being oriented relative to the neck channel such that the user's upper cervical spine resides in a substantially or fully relaxed non-extended state and the user's mandible is maintained in a substantially or fully closed position, and wherein the relative angle at which the chin region reaches laterally outward from the neck channel is no greater than 120-degrees.

2. The apparatus of claim 1 further comprising one or more toppers each comprising a resiliently compressible material of greater compressibility than said pillow, including a first topper for placement on the top surface of said pillow in overlying relation to the head recess therein.

3. The apparatus of claim 2 wherein the pillow comprises an additional head recess and additional neck channel both recessed in the bottom surface of the pillow, and said one or more toppers includes a second topper for placement on the bottom surface of said pillow in overlying relation to the additional head recess therein.

4. The apparatus of claim 1 wherein a depth of the head recess at the chin region thereof is at least 1-inch.

5. The apparatus of claim 4 wherein the depth of each head recess at the chin region thereof is at least 2-inches.

6. The apparatus of claim 1 wherein the pillow comprises a multi-layer construction comprising a first piece having a head-shaped cutout therein forming the peripheral area of the head recess, and an underlying second piece beneath the first piece and defining the bottom area of the head recess.

7. A method of manufacturing the apparatus of claim 6 comprising cutting the head-shaped cutout in the first piece, and then bonding the first and second pieces together.

8. The apparatus of claim 1 wherein the relative angle at which the chin region reaches laterally outward from the neck channel is no greater than 110-degrees.

9. The apparatus of claim 1 wherein the relative angle at which the chin region reaches laterally outward from the neck channel is no greater than 100-degrees.

10. The apparatus of claim 1 wherein the relative angle at which the chin region reaches laterally outward from the neck channel is at least 80-degrees.

11. The apparatus of claim 1 wherein a relative angle between an axis of the neck channel and the front surface of the pillow is between 80 and 100 degrees.

12. The apparatus of claim 1 wherein a relative angle between an axis of the neck channel and the front surface of the pillow is between 85 and 95-degrees.

13. An apparatus for treating snoring and/or sleep apnea, said apparatus comprising:
- a pillow having:
  - a front surface;
  - a rear surface opposite the front surface;
  - a left side surface;
  - a right side surface opposite the left side surface;
  - a bottom surface;
  - a top surface opposite the bottom surface;
  - a head recess formed in the top surface, the head recess comprising:
    - a bottom area for receiving and supporting a lateral side of a user's face, and
    - a peripheral area spanning upwardly to the top surface of the pillow from the bottom area of the head recess at a perimeter thereof; and
  - a neck channel recessed in the top surface and extending from the head recess toward the front surface of the pillow to receive and support a lateral side of the user's neck; and
- one or more toppers each comprising a resiliently compressible material of greater compressibility than said pillow, including a first topper for placement on the top surface of said pillow in overlying relation to the head recess therein;

wherein:
the peripheral area of the head recess includes a chin region reaching laterally outward from the neck channel at a relative angle thereto toward one of the left and right side surfaces of the pillow for receipt of an underside of the user's chin against said chin region, said chin region being oriented relative to the neck channel such that the user's upper cervical spine resides in a substantially or fully relaxed non-extended state and the user's mandible is maintained in a substantially or fully closed position; and
the pillow comprises a shoulder recess formed in the front surface for receiving one of the user's shoulders, the neck channel spans between the head recess and the shoulder recess, and the first topper is sized and shaped to include a portion thereof that overlies the shoulder recess.

14. The apparatus of claim 13 wherein the pillow comprises an additional head recess and additional neck channel both recessed in the bottom surface of the pillow, said one or more toppers includes a second topper for placement on the bottom surface of said pillow in overlying relation to the additional head recess therein, the additional neck channel spans between the additional head recess and the shoulder recess, and the second topper is sized and shaped to include a portion thereof that also overlies the shoulder recess.

15. The apparatus of claim 13 further comprising a cover having an interior space sized and shaped for receipt of both the pillow and the one or more toppers within said cover.

16. The apparatus of claim 13 wherein at least one of said one or more toppers has a uniform thickness.

17. An apparatus for treating snoring and/or sleep apnea, said apparatus comprising a pillow having:
- a front surface;
- a rear surface opposite the front surface;
- a left side surface;
- a right side surface opposite the left side surface;
- a bottom surface;
- a top surface opposite the bottom surface;
- a first head recess formed in the top surface, the head recess comprising:
  - a bottom area for receiving and supporting a lateral side of a user's face, and
  - a peripheral area spanning upwardly to the top surface of the pillow from the bottom area of the first head recess at a perimeter thereof; and
- a first neck channel recessed in the top surface and extending from the first head recess toward the front surface of the pillow to receive and support a lateral side of the user's neck;

wherein:
the peripheral area of the first head recess includes a chin region reaching laterally outward from the first neck channel at a relative angle thereto toward one of the left and right side surfaces of the pillow for receipt of an underside of the user's chin against said chin region, said chin region being oriented relative to the first neck channel such that the user's upper cervical spine resides in a substantially or fully relaxed non-extended state and the user's mandible is maintained in a substantially or fully closed position; and
the pillow also comprises:
- a second head recess and second neck channel recessed in the top surface of the pillow and being of matching configuration to the first head recess and first neck channel, among which the chin regions of the first and second head recesses each reach toward a nearest one of either the left side surface of the pillow or the right side surface of the pillow;
- a third head recess and third neck channel of matching configuration to the first head recess and first neck channel, but recessed in the bottom surface of the pillow; and
- a fourth head recess and fourth neck channel of matching configuration to the first head recess and first neck channel, but recessed in the bottom surface of the pillow;

wherein the chin regions of the third and fourth head recesses each reach toward a furthest one of either the left side surface of the pillow or the right side surface of the pillow.

18. An apparatus for treating snoring and/or sleep apnea, said apparatus comprising:
- a first pillow having:
  - a front surface;
  - a rear surface opposite the front surface:
  - a left side surface;
  - a right side surface opposite the left side surface;
  - a bottom surface;
  - a top surface opposite the bottom surface;

a first head recess formed in the top surface, the first head recess comprising:
 a bottom area for receiving and supporting a lateral side of a user's face, and
 a peripheral area spanning upwardly to the top surface of the pillow from the bottom area of the first head recess at a perimeter thereof; and
a first neck channel recessed in the top surface and extending from the first head recess toward the front surface of the pillow to receive and support a lateral side of the user's neck, wherein the peripheral area of the first head recess includes a chin region reaching laterally outward from the first neck channel at a relative angle thereto toward one of the left and right side surfaces of the pillow for receipt of an underside of the user's chin against said chin region, said chin region being oriented relative to the first neck channel such that the user's upper cervical spine resides in a substantially or fully relaxed non-extended state and the user's mandible is maintained in a substantially or fully closed position;
a second head recess and second neck channel recessed in the top surface of the first pillow and being of matching configuration to the first head recess and first neck channel; and
a second pillow that has a third head recess and third neck channel that are of matching configuration to first head recess of the first pillow, and also has a fourth head recess and a fourth neck channel that are also of matching configuration to the first head recess of the first pillow; and wherein the chin regions of the first and second head recesses each reach toward a nearest one of either the left side surface of the pillow or the right side surface of the pillow, and wherein the chin regions of the third and fourth head recesses each reach toward a furthest one of either the left side surface of the pillow or the right side surface of the pillow.

* * * * *